United States Patent [19]

Hutchin et al.

[11] Patent Number: 5,488,165
[45] Date of Patent: Jan. 30, 1996

[54] PROCESS FOR THE PRODUCTION OF METHYL AMINES

[75] Inventors: Graham J. Hutchin, Osmotherley, England; Themistoclis Themistocleous, Bryanston; Richard G. Copperthwaite, Johannesburg, both of South Africa

[73] Assignee: Zeofuels Research (Proprietary) Limited, Transvaal, South Africa

[21] Appl. No.: 815,626

[22] Filed: Dec. 30, 1991

Related U.S. Application Data

[62] Division of Ser. No. 683,412, Apr. 10, 1991, abandoned.

[30] Foreign Application Priority Data

Apr. 10, 1990 [ZA] South Africa .................. 90/2721

[51] Int. Cl.$^6$ ............................................. C07C 209/16
[52] U.S. Cl. ................................. 564/479; 564/463
[58] Field of Search ....................... 564/479, 463

[56] References Cited

U.S. PATENT DOCUMENTS

| | | | |
|---|---|---|---|
| 3,367,884 | 2/1968 | Reid Jr. ........................ | 502/78 |
| 3,553,278 | 1/1971 | Sato et al. .................... | 502/64 |
| 3,907,711 | 9/1975 | Riley et al. .................. | 423/328 |
| 4,059,543 | 11/1977 | Kiovsky et al. .............. | 502/60 |
| 4,254,061 | 3/1981 | Weigert ........................ | 564/479 |
| 4,623,529 | 11/1986 | Sanders et al. .............. | 423/328 |
| 4,918,233 | 4/1990 | Deeba et al. ................. | 564/479 |
| 4,983,560 | 1/1991 | Copperthwaite et al. ...... | 502/85 |

FOREIGN PATENT DOCUMENTS

| | | | |
|---|---|---|---|
| 0025693 | 3/1981 | European Pat. Off. . | |
| 0130407 | 1/1985 | European Pat. Off. . | |
| 307239 | 3/1989 | European Pat. Off. ......... | 423/328 |
| 55-47143 | 4/1980 | Japan .......................... | 423/328 |
| 641983 | 1/1979 | U.S.S.R. ..................... | 502/85 |
| 284245 | 5/1929 | United Kingdom ........... | 502/85 |

OTHER PUBLICATIONS

Bauer et al. "Molecular Sieve Sorbents from Clinoptilolite" Can. J. Chem. 42(1964) pp. 1481–1487.

*Primary Examiner*—Glennon H. Hollrah
*Assistant Examiner*—Scott C. Rand
*Attorney, Agent, or Firm*—Cushman Darby & Cushman

[57] ABSTRACT

A modified natural clinoptilolite, produced by treating a natural clinoptilolite with a suitable mineral acid or with a suitable alkali and then with a suitable mineral acid, is used as a catalyst in a process for the conversion of methanol and ammonia to give a product containing at least 50% by weight of monomethylamine.

6 Claims, No Drawings

PROCESS FOR THE PRODUCTION OF METHYL AMINES

This is a division of Application No. 07/683,412, filed on Apr. 10, 1991, which was abandoned upon the filing hereof.

BACKGROUND OF THE INVENTION

This invention relates to a modified natural clinoptilolite for use as a catalyst in a process for the conversion of methanol and ammonia to methyl amines, and to a method for the conversion of methanol and ammonia using the catalyst.

Methyl amines, particularly monomethylamine and dimethylamine, are important chemical intermediates for use as starting materials for the manufacture of various solvents, pharmaceuticals, organic rubbers and surfactants. There is therefore a need to identify improved manufacturing processes for these chemicals. Methyl amines are generally produced by reacting methanol with ammonia in the gas phase at an elevated temperature (250° C.–400° C.) in the presence of a suitable catalyst. For example, a mixture of monomethylamine, dimethylamine and trimethylamine can be produced by reacting ammonia and methanol over a mixture of zinc chloride and ammonium chloride as catalyst at 300° C. (see J D Roberts and M C Caserio in "Basic Principles of Organic Chemistry", p. 654, W A Benjamin, New York 1965).

In general, acidic catalysts give the best conversions. The main problem with this process is that the reaction produces an equilibrium mixture of the different methyl amines with the trimethylamine being the most thermodynamically favoured product. This is unfortunate since commercially the trimethylamine is the least desired product. More recently the use of crystalline aluminosilicates (known as zeolites), as catalysts has been found to produce mixtures of amines rich in the more commercially valuable dimethylamines. For example, L Abrams, T E Gier, P D Shannon and G C Sonnischen have disclosed (in European Patent Application No. 183423) that methanol and ammonia can be reacted at 250° C.–450° C. and 1 atmosphere pressure over the zeolites rho, ZK-5 or chabazite (sometimes exchanged with $H^+$ or alkali metal ions) to give dimethylamine as the major product. R N Cochran has also disclosed (in European Patent Application No. 85408 and U.S. Pat. No. 4,398,041) that crystalline aluminosilicates catalyse the reaction of methanol with ammonia to form methyl amines. The preferred crystalline aluminosilicate zeolites are the hydrogen form of erionite or macroporous chabazite/erionite mixtures in the hydrogen form. K M Minnachev, A I Maksimov, I V Mishin and I I Leviskii have demonstrated (in the Russian Journal Dokl. Acad. Nauk. SSSR, 1985, volume 280, part 5, pages 1154–9) that butanol can be reacted with ammonia using a range of zeolites as catalysts at 400° C. to form mainly monobutylamine and dibutylamine together with traces of tributylamine. The faujasite type zeolite Y in the sodium form was found to give the best results whereas the sodium form of zeolite A gave the poorest results. In addition a number of studies have shown that the pentasil zeolites, e.g. zeolite ZSM-5, can also be used as catalysts for the synthesis of methyl amines.

Other relevant references include U.S. Pat. No. 4,806,689 which discloses the production of dimethylamine by reacting methanol or dimethylether and ammonia in the presence of a catalytic amount of acidic zeolite rho;

U.S. Pat. No. 4,752,596 which discloses the production of dimethylamine by reacting methanol or dimethylether and ammonia in the presence of a catalyst which is an acidic zeolite selected from chabazite, eriomite, ZK-5 and rho optionally modified by treatment with compounds containing silicon, aluminium, phosphorous or boron;

Japanese Patent Application No. 90027335 which discloses the preparation of methylamine by reacting methanol and ammonia in the presence of a mordenite type zeolite; and an article in J Catal. 1990, vol 124,.No. 1, pages 268 to 280 which discloses designing zeolite catalysts for shape-selective reactions, and chemical modification of surfaces for improved selectivity to dimethylamine in synthesis from methanol and ammonia.

Under conditions normally employed with commercial catalysts, the aforementioned zeolites tend to produce mixtures of alkyl amines. The chemical industry would prefer a catalyst that has high specificity to a desired product, e.g. monomethylamine, since this would reduce product separation and manufacturing costs. Furthermore, the chemical industry would prefer a catalyst that is relatively inexpensive and this is not readily achieved if synthetic zeolites are utilised.

SUMMARY OF THE INVENTION

According to a first aspect of the invention there is provided a modified natural clinoptilolite for use as a catalyst in a process for the conversion of methanol and ammonia to methyl amines wherein 50% or more by weight, preferably 70% or more by weight, more preferably 90% or more by weight of the methyl amines is monomethylamine.

The modified natural clinoptilolite may be produced starting from any suitable natural clinoptilolite such as that from Zululand, South Africa, or that from Futatsui, Japan, by any suitable modification process. Various modification processes are set out below.

According to a second aspect of the invention there is provided a process for the conversion of methanol and ammonia to give a product containing at least 50% by weight, preferably at least 70% by weight, more preferably at least 90% by weight of monomethylamine in a reactor in the presence of a modified natural clinoptilolite which includes the steps of:

(a) feeding the methanol and the ammonia to the reactor containing the catalyst;

(b) converting the methanol and the ammonia in the reactor in the presence of the catalyst at a temperature of from 300° C. to 500° C. inclusive, preferably from 350° C. to 450° C. inclusive, and at a pressure from 1 to 20 atmospheres inclusive, preferably from 1 to 10 atmospheres inclusive, more preferably from 1 to 3 atmospheres inclusive; and (c) recovering the product.

DESCRIPTION OF EMBODIMENTS

The first aspect of the invention is a modified natural clinoptilolite for use as a catalyst in a process for the conversion of methanol and ammonia to methyl amines where 50% or more by weight, preferably 70% or more by weight, more preferably 90% or more by weight of the methyl amines is monomethylamine.

There are various processes by which the natural clinoptilolite may be modified to render it suitable for use as a catalyst, and these processes are set out below.

The first method is that disclosed in an article in Applied Catalysis, 16 (1985) 249–253, by Sakoh, Nitta and Aomura. This article discloses two methods for the modification of a natural clinoptilolite from Futatsui, Japan. The first method involves treating the natural clinoptilolite with 1M HCl at 80° C. for 24 hours after which the sample is filtered off, washed with distilled water and dried in air. The second method involves impregnating the clinoptilolite with 0,05M and 0,5M $H_2SO_4$, whereafter the samples are filtered off, dried in air and then calcined at 400° C. for 3 hours in air. These catalysts were utilised in the conversion of methanol to light olefins in a fixed bed continuous flow reactor under atmospheric pressure.

The second method is disclosed in South African Patent No. 88/6733. This patent discloses a method for the modification of a natural clinoptilolite to produce a modified clinoptilolite for use in a reaction for the preparation of or transformation of hydrocarbons which method includes the step of treating the natural clinoptilolite with a suitable mineral acid such as hydrochloric acid at a concentration of greater than 1M, preferably from greater than 1M up to and including 2,5M, more preferably 2M, for a treatment time of longer than 24 hours, and at a suitable treatment temperature, preferably of from 40° C. to 80° C., to produce the modified clinoptilolite. Further, after the acid treatment step, the clinoptilolite is preferably calcined at a suitable calcining temperature, e.g. from 450° C. to 550° C., more preferably 500° C., for a suitable calcining time, e.g. 3 or 4 hours. The modified catalyst so produced may be used in a process for the conversion of methanol and/or dimethyl ether to hydrocarbon reaction products, and in a process for the cracking of hydrocarbon products.

The third method is disclosed in South African Patent No. 89/3131. This patent discloses a method for the modification of a natural clinoptilolite to produce a modified clinoptilolite for use in a reaction for the preparation of hydrocarbons, which method includes the step of treating the natural clinoptilolite with a phosphorous containing acid such as phosphoric acid, pyrophosphoric acid, metaphosphoric acid, hypophosphorous acid, phosphorous acid or pyrophosphorous acid, at a concentration of 0,5M or greater, preferably from 0,5M up to and including 2M, for a treatment time of equal to or longer than 24 hours, preferably up to and including 96 hours, and at a suitable treatment temperature, preferably of from 40° C. to 80° C. inclusive, to produce the modified clinoptilolite. After the acid treatment step, the modified clinoptilolite may be calcined at a suitable calcining temperature of from 400° C. to 550° C. for a suitable calcining time from 3 hours, more preferably 4 hours. The modified clinoptilolite so produced may be used in a process for the conversion of methanol and/or dimethyl ether to hydrocarbon reaction products.

The fourth method is disclosed in South African Patent No. 89/3132. This patent discloses a method for the modification of a natural zeolite to produce a modified zeolite for use in a reaction for the transformation of hydrocarbons which method includes the steps of treating the natural zeolite with a suitable alkali such as sodium hydroxide at a concentration greater than 0,5M preferably a concentration from 0,5M up to and including 5M, more preferably 2M, for a treatment time of longer than 1 hour preferably up to and including 48 hours, and at a suitable treatment temperature preferably from 30° C. to 80° C. inclusive, washing the resulting product, and treating the resulting product with a suitable mineral acid such as hydrochloric acid at a concentration of greater than 0,1M preferably a concentration from longer than 0,1M up to and including 2M, for a treatment time of longer than 1 hour, preferably up to and including 48 hours, and at a suitable treatment temperature preferably from 40° C. to 80° C. inclusive, to produce the modified zeolite. Thereafter, the modified zeolite is preferably calcined at a suitable calcining temperature of from 400° C. to 500° C. for a suitable calcining time from 3 hours.

In terms of the present invention, the natural clinoptilolite may be modified by any of the methods described above or by any other suitable known method. The modified clinoptilolite may be produced starting from a natural clinoptilolite mined in Zululand, South Africa, or Fututsui, Japan. or from any other suitable natural clinoptilolite.

The second aspect of the invention is a process for the conversion of methanol and ammonia to give a product containing at least 50% by weight of monomethylamine in a reactor in the presence of a modified natural clinoptilolite which includes the steps of:

(a) feeding the methanol and the ammonia to the reactor containing the catalyst;

(b) converting the methanol and the ammonia in the reactor in the presence of the catalyst at a temperature of from 300° C. to 500° C. inclusive, preferably from 350° C. to 450° C. inclusive, and at a pressure of from 1 to 20 atmospheres inclusive, preferably from 1 to 10 atmospheres inclusive, more preferably from 1 to 3 atmospheres inclusive; and (c) recovering the product.

The conversion of methanol and ammonia to methyl amines is well known and may be carried out according to the method of the present invention using the known reaction conditions.

The reaction will generally be carried out in a fixed bed or a fluidized bed reactor at the temperatures and pressures mentioned above.

The flow rates of starting reagents is determined by the economics of the process but generally, the ammonia to methanol ratio should be greater than 1 and preferably greater than 2.

The crux of the use of the modified clinoptilolite of the invention is that high selectivity to the desired monomethylamine can be achieved at high conversions of the reagents together with minimal formation of other methyl amines or hydrocarbon products.

An example of the use of a modified clinoptilolite as a catalyst for the process of conversion of methanol and ammonia to methyl amines will now be given.

EXAMPLE

A sample (50 g) of unmodified natural clinoptilolite, obtained from Zululand, South Africa, was suspended with stirring in a solution (500 ml) of 2M sodium hydroxide at 50° C. for eight hours. Following this treatment the sample was collected by filtration and washed with de-ionised water. The sample was then suspended with stirring in 500 ml of 0,5M aqueous hydrochloric acid at 60° C. for 15 hours. The sample was collected by filtration and washed with de-ionised water, and dried at 120° C. for 4 hours and then calcined at 400° C. Following this treatment, the modified clinoptilolite was found to have a surface area of 46 $m^2g^{-1}$ by the BET method. The modified clinoptilolite was then used as a catalyst for the conversion of methanol and ammonia to methyl amines in a fixed bed downflow microreactor. Methanol and ammonia were reacted over the zeolite at a methanol weight hourly space velocity (WHSV) of O,O74 $h^{-1}$ and a methanol:ammonia molar ratio of 1:3.

The reactor temperature was initially 300° C. and this was subsequently raised to 350° C., then 400° C. and finally 450° C. Products were collected and analysed by standard gas chromatographic techniques. The results, given in Table 1, demonstrate that the modified clinoptilolite is a particularly effective catalyst for the conversion of methanol and ammonia to monomethylamine. Further experiments showed that in the absence of the modified clinoptilolite catalyst no significant conversion of these reagents to useful products could be achieved.

TABLE 1

Conversion of Methanol and Ammonia over Modified Clinoptilolite Catalyst Prepared as Described in the Example

| REACTOR TEMPERATURE$^a$ (°C.) | 300 | 350 | 400 | 450 |
|---|---|---|---|---|
| Conversion | 24,3 | 74,2 | 96,3 | 97,7 |
| Selectivity (% by mass) | | | | |
| Amines | | | | |
| Monomethylamine | 93,9 | 84,0 | 90,2 | 73,1 |
| Dimethylamine | 0 | 3,2 | 7,6 | 19,4 |
| Trimethylamine | 0 | 10,5 | 0 | 1,4 |
| Hydrocarbons | | | | |
| Methane | 0,1 | 0,2 | 0,2 | 1,0 |
| Ethene | 0,8 | 0,1 | 0,1 | 0,4 |
| Ethane | 0 | 0 | 0 | 0,1 |
| Propene | 0 | 0 | 0 | 0,5 |
| Propane | 0 | 0 | 0 | 0 |
| Butanes and Butenes | 4,9 | 1,6 | 0,6 | 0,2 |
| Pentanes and Pentenes | 0 | 0,3 | 1,2 | 3,0 |
| Higher hydrocarbons | 0 | 0 | 0 | 0,8 |

$^a$Methanol WHSV = 0,074 h$^{-1}$, methanol:ammonia molar ratio = 1:3

We claim:

1. A process for the conversion of methanol and ammonia to give a product containing at least 70% by weight of monomethylamine in a reactor in the presence of a modified natural clinoptilolite catalyst produced by treating a natural clinoptilolite with either (1) a mineral acid at a concentration of greater than 1M for a treatment time of longer than 24 hours and at a treatment temperature of from 40° C. to 80° C. inclusive; or (2) an alkali at a concentration greater than 0.5M for a treatment time of longer than 1 hour at a treatment temperature of from 30° C. to 80° C. inclusive, washing the resulting product, and treating the resulting product with a mineral acid at a concentration of greater than 0.1M for a treatment time of longer than 1 hour and at a treatment temperature of from 40° C. to 80° C. inclusive which includes the steps of:

(a) feeding the methanol and ammonia to the reactor containing the catalyst;

(b) converting the methanol and the ammonia in the reactor in the presence of the catalyst at a temperature of from 300° C. to 500° C. inclusive, and at a pressure of from 1 to 20 atmospheres inclusive; and (c) recovering the product.

2. A process according to claim 1 wherein 90% or more by weight of the methyl amines is monomethylamine.

3. A process according to claim 1 wherein the modified clinoptilolite is produced by treating the natural clinoptilolite with hydrochloric acid at a concentration of from greater than 1M up to and including 5M for a treatment time of longer than 24 hours and at a treatment temperature of from 40° C. to 80° C. inclusive.

4. A process according to claim 1 wherein the modified clinoptilolite is produced by treating a natural clinoptilolite with sodium hydroxide at a concentration of from greater than 0,5M up to and including 5M, for a treatment time of longer than 1 hour up to and including 48 hours and at a treatment temperature of 30° C. to 80° C. inclusive, washing the resulting product, and treating the resulting product with hydrochloric acid at a concentration of greater than 0,1M up to and including 2M for a treatment time of longer than 1 hour up to and including 48 hours and at a treatment temperature of from 40° to 80° C.

5. A process according to claim 1 wherein the modified clinoptilolite is calcined at a calcining temperature of from 400° C. to 500° C. inclusive for a calcining time of from 3 hours.

6. A process according to claim 1 wherein the modified natural clinoptilolite is produced starting from a natural clinoptilolite from Zululand, South Africa.

* * * * *

UNITED STATES PATENT AND TRADEMARK OFFICE
CERTIFICATE OF CORRECTION

PATENT NO. : 5,488,165
DATED : January 30, 1996
INVENTOR(S) : Hutchings et al

It is certified that error appears in the above-indentified patent and that said Letters Patent is hereby corrected as shown below:

On the title page item,
[75] Inventors:  Graham J. Hutchings, Osmotherley, England; Themistoclis Themistocleous, Bryanston; Richard G. Copperthwaite, Johannesburg, both of South Africa Signed and Sealed this Twenty-fifth Day of June, 1996

Attest:

BRUCE LEHMAN

*Attesting Officer*   *Commissioner of Patents and Trademarks*